(12) United States Patent
Liao et al.

(10) Patent No.: US 6,780,899 B2
(45) Date of Patent: Aug. 24, 2004

(54) HOMOPOLYMERS CONTAINING STABLE ELASTICITY INDUCING CROSSLINKERS AND OCULAR IMPLANTS MADE THEREFROM

(75) Inventors: Xiugao Liao, Irvine, CA (US); Vijay Gulati, Lake Forest, CA (US)

(73) Assignee: Medennium, Inc., Irvine, CA (US)

( * ) Notice: Subject to any disclaimer, the term of this patent is extended or adjusted under 35 U.S.C. 154(b) by 0 days.

(21) Appl. No.: 10/279,555

(22) Filed: Oct. 24, 2002

(65) Prior Publication Data

US 2004/0034118 A1 Feb. 19, 2004

Related U.S. Application Data

(63) Continuation of application No. 09/865,845, filed on May 25, 2001, now abandoned, which is a continuation of application No. 09/383,837, filed on Aug. 26, 1999, now Pat. No. 6,271,281.

(51) Int. Cl.$^7$ ............................... A61F 2/14; A61F 2/16
(52) U.S. Cl. ............................... 523/106; 623/5; 623/6; 351/160 H
(58) Field of Search ............................... 523/106; 623/5, 623/6; 351/160 H

(56) References Cited

U.S. PATENT DOCUMENTS

| | | |
|---|---|---|
| 1,980,483 A | 11/1934 | Hill |
| 2,008,719 A | 7/1935 | Kuettel |
| 2,084,399 A | 6/1937 | Kuettel |
| 2,129,663 A | 9/1938 | Barrett |
| 2,500,728 A | 3/1950 | Williams |
| 2,594,560 A | 4/1952 | Howard, Jr. |
| 3,153,022 A | 10/1964 | Calkins et al. |
| 3,288,771 A | 11/1966 | MacKenzie et al. |
| 3,356,663 A | 12/1967 | Loversidge et al. |
| 3,405,088 A | 10/1968 | Slocum |
| 3,427,262 A | 2/1969 | Corte et al. |
| 3,852,177 A | 12/1974 | Atchison et al. |
| 3,862,096 A | 1/1975 | Kitamura et al. |
| 3,963,685 A | 6/1976 | Abrahams |
| 4,258,204 A | 3/1981 | Banks et al. |
| 4,306,780 A | 12/1981 | Tarumi et al. |
| 4,486,489 A | 12/1984 | George |
| 4,518,756 A | 5/1985 | Yoshida et al. |
| 4,578,504 A | 3/1986 | Hammar |
| 4,668,446 A | 5/1987 | Kaplan et al. |
| 4,676,792 A | 6/1987 | Praeger |
| 4,704,006 A | 11/1987 | Sakagami et al. |
| 4,761,438 A | 8/1988 | Komiya et al. |
| 4,834,750 A | 5/1989 | Gupta |
| 4,946,469 A | 8/1990 | Sarfarazi |
| 4,977,229 A | 12/1990 | Culberson et al. |
| 5,037,435 A | 8/1991 | Chang et al. |
| 5,041,511 A | 8/1991 | Yanagawa et al. |
| 5,217,491 A | 6/1993 | Vanderbilt |
| 5,258,024 A | 11/1993 | Chavel et al. |
| 5,269,813 A | 12/1993 | Yoshida et al. |
| 5,270,360 A | 12/1993 | Solomon |
| 5,290,892 A | 3/1994 | Namdaran et al. |
| 5,331,073 A | 7/1994 | Weinschenk, III et al. |
| 5,346,978 A | 9/1994 | Baron et al. |
| 5,359,021 A | 10/1994 | Weinschenk, III et al. |
| 5,387,661 A | 2/1995 | Frost |
| 5,389,722 A | 2/1995 | Nagasuna et al. |
| 5,393,644 A | 2/1995 | Etzbach et al. |
| 5,403,901 A | 4/1995 | Namdaran et al. |
| 5,556,931 A | 9/1996 | Imura et al. |
| 5,603,774 A | 2/1997 | LeBoeuf et al. |
| 5,608,471 A | 3/1997 | Miller |
| 5,654,350 A | 8/1997 | Nunez et al. |
| 5,674,960 A | 10/1997 | Namdaran et al. |
| 5,681,871 A | 10/1997 | Molock et al. |
| 5,693,095 A | 12/1997 | Freeman et al. |
| 5,789,463 A | 8/1998 | Odagiri et al. |
| 5,814,680 A | 9/1998 | Imafuku et al. |
| 5,821,306 A | 10/1998 | Hodd |
| 5,849,841 A | 12/1998 | Mühlebach et al. |
| 5,855,825 A | 1/1999 | Ito |
| 5,856,370 A | 1/1999 | Chmelir |
| 5,861,031 A | 1/1999 | Namdaran et al. |
| 5,891,931 A | 4/1999 | Leboeuf et al. |
| 5,922,821 A | 7/1999 | LeBoeuf et al. |
| 6,271,281 B1 | 8/2001 | Liao et al. |

FOREIGN PATENT DOCUMENTS

| | | |
|---|---|---|
| EP | 0 265 399 A2 | 4/1988 |
| JP | 277208 | 10/1987 |
| WO | WO 98/18410 | 5/1998 |
| WO | WO 99/07756 | 2/1999 |
| WO | WO 99/53348 | 10/1999 |
| WO | WO 00/26698 | 5/2000 |

*Primary Examiner*—Tae H. Yoon
(74) *Attorney, Agent, or Firm*—Frost Brown Todd LLC

(57) ABSTRACT

Ocular implants composed of homopolymers containing stable elasticity inducing crosslinkers which contain rigid chemical groups disposed between at least two polymerizable ethyleneically unsaturated chemical groups are disclosed. These ocular implants are stable, elastic, soft, optically clear, have high refractive index and low-tack surfaces.

7 Claims, 1 Drawing Sheet

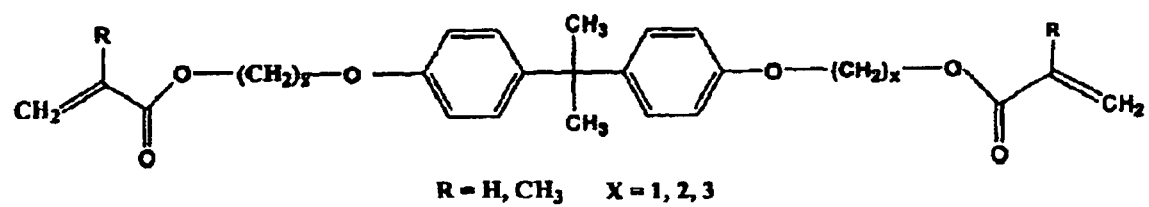
1. Elasticity inducing, rigid crosslinker
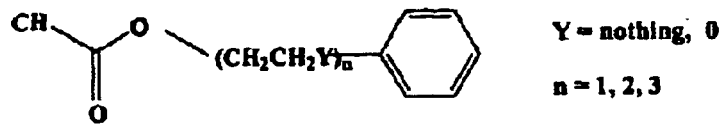
2. Preferred monomer structure
Fig. 1. Preferred Embodiments of Elasticity Inducing, Rigid Crosslinkers and Monomers

HOMOPOLYMERS CONTAINING STABLE ELASTICITY INDUCING CROSSLINKERS AND OCULAR IMPLANTS MADE THEREFROM

CROSS REFERENCE TO RELATED APPLICATION

This application is a continuation of U.S. patent application Ser. No. 09/865,845, filed May 25, 2001 ABN, which was a continuation of U.S. patent application Ser. No. 09/383,837, filed Aug. 26, 1999, now U.S. Pat. No. 6,271,281.

FIELD OF INVENTION

The present invention broadly relates to ocular implants. Specifically, it relates to ocular implants made from homopolymers containing chemical crosslinkers for interlinking polymer chains. More specifically, the present invention is directed to ocular implants made from homopolymers containing chemical crosslinkers having the unique ability to produce stable elasticity in these homopolymers in conjunction with the production of other unique combinations of chemical and physical properties. The present invention is particularly well suited to the production of elastomeric, soft, optically clear, high refractive index, low tack homopolymers and to medical devices, including intraocular lenses, corneal implants, corneal overlays, and phakic retractive lenses, made from such homopolymers.

BACKGROUND

Generally speaking, "polymers" are commonly understood to be any of a wide variety of synthetically produced, nonmetalic or organic compounds which can be molded into various forms and hardened for commercial use. They are made from high molecular weight macromolecules produce by "polymerizing" or chemically linking individual chemical sub-units or "monomers." There are essentially two types of polymers: homopolymers and copolymers. "Homopolymers" are made up of identical, repeating monomers chemically bonded together into polymer chains of various lengths. "Copolymers" are made from combinations of at least two different monomers which are polymerized to form chains of alternating different monomers or chains where the different monomers are randomly dispersed throughout.

There are both naturally occurring and synthetically produced polymers. Examples of natural polymers include, among others, proteins, polysaccharides, deoxyribose nucleic acid (DNA) and rubber, wherein the individual monomer sub-units are, respectively, amino acids, sugars, nucleic acids, and isoprene. Common synthetic polymers, which include plastics and silicones, are made from highly chemically reactive monomers including styrenes, acrylates, silanols and many others. Synthetic polymers have become one of the most important classes of molecules since their invention at the turn of the twentieth century. They have had a significant impact on every aspect of human life. However, significant efforts are continually underway to further our understanding of, and to advance the science of polymer chemistry. These efforts include the development of critically needed superior polymeric materials having presently unavailable combinations of physical and chemical properties.

The physical and chemical properties of both homopolymers and copolymers are dictated by the extent and the nature of polymer chain interactions within the polymers themselves. These interactions are, in turn, a function of the individual monomeric sub-units' sizes, weights, charges and chemical structures. The most important types of interactions between polymer chains are those chemical interactions which result in what is know in the art as "crosslinking." Crosslinking can be defined as a chemical process which joins individual polymer chains together by forming chemical bridges between and among the polymer chains. These "crosslinks" lock the polymer chains together into immense single molecules wherein the individual polymer chains can no longer slip over or relative to one another.

There are essentially two mechanisms by which polymers can be crosslinked. The first crosslinking method utilizes an external energy source, such as high energy radiation or heat, to induce interactions between chemically reactive functional groups within the individual monomers of each polymer chain forming new chemical bonds between the polymer chains. Polymers crosslinked using such an external energy source must be composed of monomers that are susceptible to such chemical reactions. Typically, such monomers have pendent, exposed chemical functional groups (portions of the monomer that are chemically reactive and extend away from the polymer chain, also referred to as "residues") which are capable of interacting with chemically compatible pendent groups on adjacent polymer chains. One example of this type of crosslinking involves the naturally occurring proteins found in animal skin. These proteins are complex polymers composed of numerous different monomers (amino acids) each containing highly reactive pendent chemical groups including sulfur, carboxylic acid and amine residues. As animals age, the cumulative effects of UV radiation (sun exposure) induce crosslinking between these protein molecules, changing the physical structure of these polymers and causing the skin to lose its natural elasticity and to become hard and wrinkled.

The second crosslinking mechanism utilizes the addition of exogenous crosslinking agents (an additional multifuctional molecule, not part of a polymer chain) in conjunction with the application of a chemical catalyst (or "accelerator") which promotes the reaction between the crosslinking agents and the chemical functional groups within the polymer chains. Such chemical reactions among polymer chains using crosslinking agents are not limited to polymers with pendent chemical groups. Rather, this form of chemical crosslinking works equally well with smaller monomer sub-units (such as "isoprene" or natural rubber) in which the only reactive functional group is a double chemical bond that is sequestered within the linear portion of the molecule (the straight part of the polymer chain, not extending from the macromolecule). Therefore, the use of crosslinking agents, either alone or in conjunction with external energy sources such as heat and radiation, provides an extremely versatile crosslinking mechanism which can produce profound changes in the polymer's properties.

One example of the dramatic changes that such exogenous crosslinking agents can produce in a polymer is the "vulcanization" of rubber. Vulcanization is the process of chemically bridging or linking the polymer's chains of natural rubber (polyisoprene) using elemental sulfur as the exogenous crosslinking agent. Heat and compounds such as peroxides, metallic oxides, and chlorinated quinones are also used to catalyze the chemical reactions between the polyisoprene chains and the sulfur. Without vulcanization, naturally occurring raw rubber is an extremely tacky, amorphous mass that will not hold a shape and is easily solubilized or dissolved by organic compounds such as gasoline, oil, and acetone. After crosslinking the raw rubber hardens and becomes less tacky, more resistant to cold induced hardening or heat induced softening, and resistant to organic solvents. This crosslinked rubber can be formed into commercial articles and products while hot and fluid, and will retain the formed shape upon cooling. Without crosslinking, natural rubber would not possess these beneficial properties required for its wide range of industrial applications including tires, shoes, electric insulators and waterproof articles.

These crosslinking techniques are commonly employed with both natural and synthetic polymers in order to create polymer compounds having optimized properties for particular applications. However, crosslinking polymers is a technically difficult process that must be precisely controlled for good results. Crosslinking agents can be simple inorganic compounds such as the sulfur used for vulcanization discussed above, or can be more complex organic compounds such as the divinyl benzene used in a wide variety of more exotic plastics. The amount of crosslinker added, the rate at which the crosslinking reaction is allowed to occur, and the density of the crosslinkable chemical functional groups present on the polymer chains all contribute to the resulting polymer's physical and chemical properties.

Consequently, the polymer chemist is faced with a series of difficult and conflicting choices that often result in compromises necessary to achieve the appropriate final compounds for a given application or purpose. Further, it is essential for the polymer chemist to understand the exact physical and chemical properties that are desired in the final polymer compounds before the crosslinking chemistry and mechanisms can be selected. Often, a process which accentuates one desirable physical property, such as polymer hardness, will have an adverse effect on another desirable property, such as surface tackiness or stickiness. Therefore, each crosslinking application requires a unique polymer formulation and an associated synthetic method for production including novel crosslinker and monomer combinations. Thus, it can be appreciated that the design and development of a polymer for a specific task is a daunting challenge that can involve completely new chemical and technological approaches.

Perhaps one of the most demanding applications for modern polymers is in the medical field, such as the field of ophthalmology which deals with the structure, function, repair of, and diseases of the eye. Where damage or disease (typically cataracts) requires the replacement of the eye's natural human lens, a polymer lens that has a unique combination of biological and physical properties is required. In addition to replacement intraocular lenses (IOLs), damaged corneas may require corneal implants or overlays. More recently, corrective medical implants known as "phakic" lenses have been proposed intended to augment or correct the light focusing function of the natural lens. Generally, the polymers used to produce such lenses and ocular implants must be optically clear, have a refractive index within the range suitable for human vision, and be biocompatible. Moreover, such implants must balance the competing physical properties of elasticity and flexibility with high strength and stability.

Early IOLs made from polymers such as polymethylmethacrylate (PMMA) were rigid and required a large incision (greater than 6 mm) in order to be inserted in the eye. This often resulted in a protracted and uncomfortable healing process which further stimulated the development of soft IOLs that could be folded and inserted through a considerably smaller opening (on the order of 4.0 mm or less) in order to reduce healing time and potential complications. However, folding an IOL for small incision implantation, though simple in theory, has been difficult to accomplish due to the strongly conflicting physical demands required of the polymers used to make such medical implants. Folding a lens for implantation significantly added to the demands placed on the polymer compounds used by requiring polymers that possess all of the previously mentioned attributes, optical clarity, non-tacky surfaces, stability and biocompatibility, among others, but by also requiring that the implant possess sufficient flexibility for folding while being sufficiently stable to resist damage and distortion induced by folding.

Initial attempts to find a polymeric compound that could be suitable for use with foldable IOLs centered around silicone monomers. Silicone polymer IOLs possessed excellent optical clarity, a suitable refractive index range, were generally biocompatible, and had excellent resilience. However, these lenses were relatively stiff and difficult to fold requiring larger than ideal incisions, special implantation tools and techniques, and have been known to unfold with nearly explosive intensity, potentially damaging delicate structures within the eye. Further, silicone implants have fallen out of favor due to latent biocompatibility concerns. As a result, a number of alternating, non-silicone organic polymers derived from acrylate and acrylate esters have been investigated and developed.

Many types of acrylate polymers have been used or proposed for foldable IOL fabrication. The majority of these proposed acrylate polymers are copolymer mixes of multiple monomers intended to produce the desired combination of properties possessed by each monomer component. However, the technical difficulties in making such soft, foldable optical polymers have been numerous, greatly slowing progress in the field. The ideal ocular implant or ocular lens, as previously stated, must be optically clear and must remain so for a prolonged period of time following implantation. The refractive index must be greater than 1.50 and the lens must be stably elastic and capable of stretching to 150% of its pre-stretch size before breaking (elongation factor). The implant must be soft enough to allow easy pre-insertion folding and it must have a non-tacky surface so that the inserted lens will unfold in a predictable manner without requiring further or difficult manipulation.

These often competing demands are extremely difficult to combine in a single material. For example, polymers with low tack surfaces are often too hard and crack when folded. Conversely, softer polymers which fold easily, are usually tacky, making them difficult to handle and complicating implantation and post insertion unfolding. Furthermore, the ideal ocular implant must have a stable elastic structure that will not be damaged, distorted, or destroyed by folding, while at the same time retaining all of the optical qualities required to function as a successful implant, lens, or corneal replacement. In spite of the almost continual advances in polymer chemistry and ocular implant design, the copolymers of the prior art have failed to yield IOLs and ocular implants having these ideal combinations of properties.

The majority of non-silicone polymers used for IOLs and ocular implants have been acrylate copolymers generally containing combinations of individual monomers in concentrations ranging from about 20 percent to 80 percent. These copolymers have been polymerized using a variety of techniques known in the art including external energy sources, exogenous crosslinkers, catalysts, and accelerators. Crosslinking, when performed, has generally been accomplished to stabilize the polymers utilizing low concentrations of low molecular weight diacryates, multifunctional esters, epoxides and diols.

In contrast to these known chemical techniques and compositions, the present inventors, have surprisingly determined that by customizing the structural configurations of their crosslinking agents in accordance with the teachings of the present invention, they can produce homopolymer materials that possess markedly superior combinations of physical and chemical properties that were previously unobtainable in presently available homopolymers and copolymers. For example, lenses made from the homopolymers of the present invention, though optically clear and remarkably elastic, are physically stable and can be cast into very thin cross-sectional structures that were previously available only with significantly harder polymers.

As a result, ocular implants including IOLs can be produced having strongly tapered peripheral borders. This is particularly important with IOLs as the present invention now makes it possible to manufacture stably elastic intraocular lenses having sharp edges. As a result, cell migration between the back of the IOL and the posterior capsule of the eye [a process that often results in posterior capsule opacification (PCO) preventing light from reaching the retina of the eye and possibly leading to blindness] is believed to be significantly reduced. Prior art intraocular lenses cast from conventional acrylate polymers cannot be manufactured with such tapered circumferential borders having sharp edges due to the instability of conventional "soft" polymers when cast into such thin configurations. Consequently, patients with IOLs made from conventional polymers may be more susceptible to cell migration and resultant PCO.

Further, as known in the art, a common, non-invasive surgical procedure for eliminating posterior capsule opacity is to use a laser, such as an Yittrium Aluminum Garnet or YAG laser, to restore the patient's vision. This procedure, known as YAG Capsulotomy, produces an incision or hole in the opacified posterior capsule which then allows the passage of light through to the retina. However, a not uncommon complication of a laser capsulotomy is lens damage that can occur if a conventional acrylate polymer IOL is inadvertently struck by the YAG laser during the capsulotomy. This can cause damage ranging from pitting of the lens to complete fracturing of the lens necessitating its surgical removal and replacement.

In contrast, IOLs made from the homopolymers of the present invention, in addition to being less susceptible to PCO, are less susceptible to laser damage as well. In the rare event that PCO does occur in association with the lenses of the present invention, it is believed that the "rubbery" consistency of the homopolymers of the present invention will render IOLs made therefrom significantly less susceptible to the damaging effects of YAG lasers. Thus, pitting and cracking from misdirected lasers will be significantly reduced. Therefore, it is believed that stably soft, elastic IOLs manufactured from the new homopolymers of the present invention will significantly reduce the occurrence of PCO as well as reduce the occurrence of lens damage from laser capsulotomies, if later required. This, in turn, will result in reduced patient discomfort and complications and in significantly reduced medical expenses.

A further advantage of the stable elastic homopolymers of the present invention is their remarkably high refractive indices. As a result, IOLs made from these homopolymers can be cast in even thinner cross-sectional shapes than were previously available without sacrificing their optical resolution. Thus, lenses produced in accordance with the teachings of the present invention can be folded into significantly smaller folded configurations, resulting in IOLs that can be inserted into the eye through smaller incisions (on the order of 3.2 to 4.0 mm) than IOLs made from known foldable polymers. Therefore, it should be appreciated by those skilled in the art that, just as the foldable silicone and acrylate polymers of the prior art represented a significant improvement over the hard, inflexible IOLs which preceded them, IOLs made from the homopolymers of the present invention provide yet another technological leap forward.

Accordingly, as will be discussed in detail herein, it is an object of the present invention to provide stably elastic, optically clear homopolymers crosslinked with rigid, structure enhancing crosslinkers.

It is another object of the present invention to provide soft, optically clear, foldable, high refractive index, IOLs that have low tack surfaces.

It is yet another object of the present invention to provide stably elastic IOLs having peripheral borders which taper to sharp edges that resists tearing or breaking.

It is another object of the present invention to provide IOLs made from "rubbery" homopolymers that are resistant to YAG laser damage.

It is still a further object of the present invention to provide stable elastic, foldable IOLs having sufficiently high refractive indices such that the IOLs can be sized to enable insertion through a truly small incision in the eye.

SUMMARY OF THE INVENTION

These and other objects are achieved by the methods, compositions, and articles of the present invention which utilize stable elasticity inducing crosslinkers containing rigid chemical groups which are disposed between at least two polymerizable ethyleneically unsaturated chemical groups to produce optically clear, high refractive index, low-tack homopolymers. When made in accordance with the teaching of the present invention, these homopolymers have unique combinations of physical and chemical properties including glass transition temperatures of equal to or less than about 15° C., refractive indices of greater than 1.50, and elongations at break of at least 150%. These stably elastic, optically clear, high refractive index, low tack homopolymers of the present invention are particularly well suited for use in medical devices such as ocular implants, including intraocular lenses (IOLs), corneal implants or overlays, and phakic lenses.

In contrast to the prior art, IOLs made from the optically clear, high refractive index, low tack homopolymers of the present invention are stably elastic and can be rolled or folded without destroying, distorting, or damaging the shape or resultant function of the lenses. The IOLs made in accordance with the teachings of the present invention can be cast in configurations having tapering peripheral borders providing the stably elastic IOLs with medically desirable sharp edges. Moreover, IOLs made in accordance with the teachings of the present invention are thinner than known foldable lenses and can be rolled or folded for insertion through small incisions in the eye of approximately 3 mm or even less. Once inserted in the eye, the low tack surfaces of the IOLs provided by the homopolymers of the present invention permit these IOLs to unfold naturally in a predictable manner thereby reducing the possibility of damage to structures within the eye or of the need for additional post insertion manipulation of the lenses by the implanting surgeon.

Generally speaking, the monomer components of the homopolymers of the present invention include, but are not limited to, phenoxyethylacrylate, poly(ethylene glycol)

phenylethylacrylate, 2-phenylethylacrylate, 3-phenylethylacrylate, 4-phenylethylacrylate and alkylacrylate derivatives.

The stable elasticity inducing rigid crosslinkers of the present invention include, but are not limited to, diacrylates and dimethacrylates of bisphenol A ethoxylate (1 EO/phenol), bisphenol A ethoxylate (2 EO/phenol), bisphenol A propoxylate (2 PO/phenol), bisphenol A, 2,2'-diallylbisphenol A, bis(4-(2-acryloylethoxy)phenyl) methane, bis(4-(2-methacryloylethoxy)phenyl)methane, bis (naphthol) A ethoxylate (X EO/naphthol), bis(2-acryloylalkylphenyl)propane, bis(2-methacryloylalkylphenyl)propane, 3,3'-(ethylenedioxy) diphenyl A ethoxylate (X EO/phenol), and naphth-diol A ethoxylate (2X EO/naphthalene), wherein X=1–5.

In one exemplary embodiment of the present invention the novel homopolymers are formulated to contain from about 95% to 99.5% monomer in conjunction with a concentration of between approximately 0.5 to 5.0% of the stable elasticity inducing crosslinkers.

In another exemplary embodiment of the present invention the homopolymers of the present invention are formulated to contain from about 97.1% to 99.5% monomer and the stable elasticity inducing crosslinkers are present in a concentration of between approximately 0.5 to 2.9%.

In yet another alternative exemplary embodiment of the present invention the uniquely stable elastic homopolymers are utilized to produce IOLs having a glass transition point equal to or below approximately 15° C., a refractive index of approximately 1.50 or greater, an elongation at break of at least approximately 150%, and are optically clear. As a result, these lenses are particularly well suited for true small incision implantation techniques and can be inserted through an incision of approximately 3.0 to 3.4 mm or less.

Further objects and advantages of the methods, compositions, and articles of the present invention which provide stable elasticity inducing crosslinkers containing rigid chemical groups to produce optically clear, high refractive index, low-tack stable elastic homopolymers suitable for use in medical devices, as well as a better understanding thereof, will be afforded to those skilled in the art from a consideration of the following detailed description of exemplary embodiments thereof taken in conjunction with the associated drawing.

BRIEF DESCRIPTION OF THE DRAWING

FIG. 1 is a diagrammatic representation illustrating the structural relationship between the elasticity inducing crosslinkers of the present invention and the monomer sub-units of the homopolymers made in accordance with the teachings of the present invention.

DETAILED DESCRIPTION OF EXEMPLARY EMBODIMENTS

The present invention provides stable elasticity inducing, rigid crosslinkers, homopolymers made therefrom, articles and medical devices including intraocular lenses, and associated methods. The homopolymers of the present invention have refractive indices of approximately 1.50 or greater, glass transition temperatures (Tg) equal to or below approximately 15° C., elongations at break of at least approximately 150%, tensile strengths greater than 250 psi, and shore hardnesses of approximately 25–45. In addition, they are stably elastic and foldable, yet are optically clear and have low tack surfaces. The stable elasticity inducing crosslinkers of the present invention are multifunctional molecules such as, but not limited to, diethyleneically unsaturated compounds containing rigid chemical groups disposed between the unsaturated groups.

The crosslinkers of the present invention contribute to providing the unique combinations of beneficial chemical and physical properties available in the homopolymers produced in accordance with the teachings of the present invention. These inventive homopolymers are ideally suited for fabricating medical devices, specifically ocular implants, and more specifically, intraocular lenses (IOLs), corneal implants or overlays, and phakic lenses. The implants made in accordance with the teachings of the present invention can be produced such that they possess a tapering circumference or peripheral boarder terminating in a desirably sharp edge. Moreover, the high refractive indices of the homopolymers of the present invention, in conjunction with the previously unavailable combinations of other beneficial physical and chemical properties, permit the production of IOLs thin enough to be inserted through incisions truly on the order of 3 mm or less, the same incision sizes as are necessary to remove the natural human lens utilizing conventional surgical techniques such as phacoemulsification.

As illustrated in FIG. 1, the stable elastic crosslinked homopolymers of the present invention can be synthesized by polymerizing a monomer 2 and then crosslinking the resulting polymer chains with a crosslinking agent 1 having at least one rigid chemical group. Examples of suitable rigid chemical groups include, but are not limited to, alkaryl, biphenyl and naphthalene groups.

The crosslinkers of the present invention have relatively high molecular weights ranging from between approximately 300 daltons to approximately 650 daltons. Non-limiting examples of these novel crosslinkers containing rigid structural groups include, but are not limited to, diacrylates and dimethacylates of bisphenol A ethoxylate (1 EO/phenol), bisphenol A ethoxylate (2 EO/phenol), bisphenol A propoxylate (2 PO/phenol), bisphenol A, 2,2'-diallylbisphenol A, bis(4-(2-acryloylethoxy)phenyl) methane, bis(4-(2-methacryloylethoxy)phenyl)methane, bis (naphthol) A ethoxylate (X EO/naphthol), bis(2-acryloylalkylphenyl)propane, bis(2-methacryloylalkylphenyl)propane, 3,3'-(ethylenedioxy) diphenyl A ethoxylate (X EO/phenol), and naphth-diol A ethoxylate (2X EO/naphthalene), wherein X=1–5.

The relatively high molecular weights of the stable elasticity inducing rigid crosslinkers of the present invention result in homopolymers having a relatively high weight percentage of crosslinker while maintaining a low crosslinking density. This permits the resulting homopolymers made in accordance with the teachings of the present invention to accrue the benefits of the crosslinker without having to introduce a crosslink density high enough to make the polymer inflexible and brittle. One of the benefits the stable elasticity inducing rigid crosslinkers of the present invention impart to the homopolymers of the present invention is enhanced hydrophobicity, or water repulsion. This reduces the surface tackiness of the homopolymers, a problem commonly associated with conventional "soft" acrylic polymers which significantly limits their utility as ocular implants by complicating their manufacture and subsequent manipulation as well as their post-implantation shape recovery.

The optically clear, high refractive index, low-tack, stable elastic homopolymers of the present invention are prepared in accordance with the teachings thereof by using the stable elasticity inducing crosslinker disclosed herein at relatively low concentrations of between approximately 0.5% to 5.0% to controllably modify the chemical and physical properties of the homopolymer. For example, these crosslinker concentrations, generally within the expected concentrations for normal or conventional crosslinkers, result in stably elastic homopolymers having an elongation at break equal to or exceeding 150%. In contrast, when the concentration of crosslinker is raised to exceed 5%, or when lower molecular weight crosslinkers are used, thus increasing crosslinking density, the resulting homopolymers become stiff and unfoldable.

It should be appreciated by those skilled in the art that, prior to the present invention, the only available techniques known to effectively produce soft, foldable polymers were to combine significant concentrations of multiple monomers, each known to possess its own beneficial properties as a homopolymer, into a single copolymer that would, hopefully, manifest a desirable combination of these multiple, individual properties. Unfortunately, these techniques rarely produced the desired results. For example, increasing a copolymer's softness or elasticity by decreasing the amount of crosslinker used generally resulted in an increase in its surface tackiness. Decreasing the surface tackiness by increasing the crosslinker concentration generally resulted in increasing the hardness of the copolymer making it stiff. Further, increasing polymer softness and elasticity generally reduced the physical stability of the copolymer such that extreme elongations greater than 100% will result in actual tearing and permanent distortions within the polymer. Meanwhile, optical clarity can be affected by variations in any of these properties. Though some in the art have tried to substitute relatively large concentrations of what are generally considered to be crosslinking compounds for use as one or more of the monomers in a copolymer mix, these efforts have been unsuccessful as well. As a result, there are very few polymeric compounds known in the art which will exhibit such desired combinations of properties and thus function as appropriate materials for ocular implants and lenses.

Therefore, unlike the prior art copolymers formed of multiple and different monomers, the individual monomers utilized to produce the novel homopolymers of the present are those whose homopolymers, made in accordance with the teachings of the present invention, have a glass transition temperature (Tg) of between approximately −40° C. to +15° C. Exemplary homopolymers suitable for practicing the present invention include, but are not limited to, phenoxyethylacrylate, poly(ethylene glycol) phenylethylacrylate, 2-phenylethylacrylate, 3-phenylethylacrylate, 4-phenylethylacrylate and alkylacrylate derivatives. Those skilled in the art can identify other suitable monomers utilizing the teachings of the present invention through routine experimentation.

In addition to the stable elasticity inducing crosslinkers of the present invention, other components can be added to the homopolymers within the scope and teachings of the present invention. These can include, but are not limited to, UV absorbing compounds and polymerization initiators. Non-limiting examples of such additional components include known UV absorbers such as acrylate, methacrylate and vinyl functionalized bezotriazoles and benzophenols. Similarly, polymerization initiating compounds that can be added to the homoploymers if desired, include, without limitation, peroxides, peroxydiacarbonates, azo free radical initiators such as azobisisobutyronitrile (AIBN), and UV initiators such as Irgacure®1850, Irgacure® 369 and Darocur®1700 (these UV initiators are products of Ciba Specialty Chemicals, Basel Switzerland).

A further understanding of the stable elasticity inducing crosslinkers, the modified homopolymers produced therefrom, the articles manufactured from the modified homopolymers, and the associated methods of the present invention will be afforded to those skilled in the art from the following non-limiting examples. Examples 1–8 demonstrate representative materials and associated methods for the fabrication of stably elastic, optically clear, high refractive index, low-tack homopolymers produced in accordance with the teachings of the present invention. Example 9 illustrates the use of exemplary novel homopolymer materials and associated methods for forming stable elastic, small incision IOLs in accordance with the teachings of the present invention.

EXAMPLE 1

A mixture containing 46.5 g of ethylene glycol phenyl ether acrylate (PEA), 3.5 g of bisphenol A ethoxylate (2 EO/phenol) dimethacrylate (BPDMA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. The molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After thepolymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.559 with a glass transition temperature of around 5–10° C.

EXAMPLE 2

A mixture containing 47.5 g of ethylene glycol phenyl ether acrylate (PEA), 2.5 g of bisphenol A ethoxylate (2 EO/phenol) dimethacrylate (BPDMA), 0.65 g of 2-(4-benzoyl-3-hydroxyphenoxy)ethyl acrylate (BHPEA), and 50 mg of azobisisobutyronitrile (AIBN) was bubbled with ultra pure nitrogen gas for 15 to 20 minutes and then transferred to sheet casting molds (molds) using a cannula under ultra-pure nitrogen gas pressure. As in Example 1, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.558 with a glass transition temperature of around 5–10° C.

EXAMPLE 3

A mixture containing 48.0 g of ethylene glycol phenyl ether acrylate (PEA), 2.0 g of bisphenol A ethoxylate (2 EO/phenol) dimethacrylate (BPDMA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. As before, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.556 with a glass transition temperature of around 5–10° C.

EXAMPLE 4

A mixture containing 48.5 g of ethylene glycol phenyl ether acrylate (PEA), 1.5 g of bisphenol A ethoxylate (2 EO/phenol) dimethacrylate (BPDMA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. The molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.557 with a glass transition temperature of around 5–10° C.

EXAMPLE 5

A mixture containing 49.0 g of ethylene glycol phenyl ether acrylate (PEA), 1.0 g of bisphenol A ethoxylate (2 EO/phenol) dimethacrylate (BPDMA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. Once again, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.558 with a glass transition temperature of around 5–10° C.

EXAMPLE 6

A mixture containing 47.5 g of ethylene glycol phenyl ether acrylate (PEA), 2.5 g of bisphenol A propoxylate (2 EO/phenol) diacrylate (BPPDA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. Again, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.558 with a glass transition temperature of around 5–10° C.

EXAMPLE 7

A mixture containing 47.5 g of ethylene glycol phenyl ether acrylate (PEA), 2.5 g of bisphenol A dimethacrylate (BPMA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. Again, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.556 with a glass transition temperature of around 5–10° C.

EXAMPLE 8

A mixture containing 47.5 g of ethylene glycol phenyl ether acrylate (PEA), 2.5 g of bisphenol A ethoxylate (2 EO/phenol) diacrylate (BPEA), 0.65 g of 2-(4-benzoyl-3-hydroxyphenoxy)ethyl acrylate (BHPEA) and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. Again, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.557 and a glass transition temperature of approximately 5–10° C.

EXAMPLE 9

A mixture containing 45.0 g of ethylene glycol phenyl ether acrylate (PEA), 5.0 g of bisphenol A ethoxylate (2 EO/phenol) dimethacrylate (BPDMA), 0.65 g of 2-(4-benzoyl-3-hydroxyphenoxy)ethyl acrylate (BHPEA), and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. Again, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.559 and a glass transition temperature of approximately 5–10° C.

EXAMPLE 10

A mixture containing 40.0 g of ethylene glycol phenyl ether acrylate (PEA), 10.0 g of bisphenol A ethoxylate (2

EO/phenol) dimethacrylate (BPDMA), 0.65 g of 2-(4-benzoyl-3-hydroxyphenoxy)ethyl acrylate (BHPEA), and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. As in Example 1, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.558 and a glass transition temperature of approximately 5–10° C.

EXAMPLE 11

A mixture containing 49.5 g of ethylene glycol phenyl ether acrylate (PEA), 0.5 g of bisphenol A ethoxylate (2 EO/phenol) dimethacrylate (BPDMA), 0.65 g of 2-(4-benzoyl-3 hydroxyphenoxy)ethyl acrylate (BHPEA), and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. As before, the molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.556 and a glass transition temperature of approximately 5–10° C.

EXAMPLE 12

A mixture containing 49.75 g of ethylene glycol phenyl ether acrylate (PEA), 0.25 g of bisphenol A ethoxylate (2 EO/phenol) dimethacrylate (BPDMA), 0.65 g of 2-(4-benzoyl-3-hydroxyphenoxy)ethyl acrylate (BHPEA), and 50 mg of azobisisobutyronitrile (AIBN) was bubbled with ultra-pure nitrogen gas for 15 to 20 minutes and then transferred to sheet casting molds (molds) using a cannula under ultra-pure nitrogen gas pressure. The molds consisted of two glass plates separated by a 2.5 mm fluorosilicone o-ring gasket secured with four clamps. The molds were filled with the monomer mixture using a double-tipped cannula. One end of the cannula was inserted through the fluorosilcone gasket of the mold and the other end was placed into a flask containing the monomer mixture. The filled molds were heated at 75° C. for a minimum of 16 hours in an oven followed by heating at 120° C. for an additional 8 hours. After the polymerization process was complete, the molds were cooled to 55° C. and held at this temperature for a minimum of 20 minutes. The molds were opened and the acrylic sheets were cured at 120° C. for 16 hours. Potentially toxic residue remaining in the fully cured acrylic sheet was removed prior to drying. The acrylic sheet was soxhelted with isopropyl alcohol for 48 hours. Following the extraction process, the acrylic sheet was removed from the soxhelting chamber, covered and transferred to a forced air oven and dried for 48 hours at room temperature. Next, the partially dried acrylic sheet was placed in a vacuum oven and heated to 45° C. under a reduced atmosphere for 24 hours, then heated at 75° C. for an additional 48 hours to complete the drying process. The resulting acrylic homopolymer was soft, had a refractive index as high as 1.557 and a glass transition temperature of approximately 5–10° C.

TABLE 1

A Summary of Examples 1–12.

| | Monomer | Crosslinkers | | | | Initiator | Properties | | | | | |
|---|---|---|---|---|---|---|---|---|---|---|---|---|
| No. | PEA | BPDMA | BPMA | BPEA | BPPDA | AIBN | RI | Tg (° C.) | Shore A | Tensile (psi) | % Elongation | Tear (lbf/in) |
| 1 | 93.00% | 7.00% | | | | 0.10% | 1.558 | | 45 | 295 | 109 | 69 |
| 2 | 95.00% | 5.00% | | | | 0.10% | 1.558 | 7.8 | 40 | 369 | 150 | 47 |
| 3 | 96.00% | 4.00% | | | | 0.10% | 1.558 | | 36 | 282 | 157 | 55 |
| 4 | 97.00% | 3.00% | | | | 0.10% | 1.558 | 7.3 | 33 | 276 | 165 | 44 |
| 5 | 98.00% | 2.00% | | | | 0.10% | 1.557 | 6.2 | 29 | 255 | 203 | 52 |
| 6 | 95.00% | | | | 5.00% | 0.10% | 1.556 | 6.6 | 35 | 255 | 157 | 43 |
| 7 | 95.00% | | 5.00% | | | 0.10% | 1.557 | | 26 | 209 | 175 | |
| 8 | 95.00% | | | 5.00% | | 0.10% | 1.558 | 6.7 | 37 | 200 | 147 | 54 |
| 9 | 90.00% | 10.00% | | | | 0.10% | 1.557 | | 51 | 192 | 80 | 36 |
| 10 | 80.00% | 20.00% | | | | 0.10% | 1.557 | | 64 | 224 | 51 | 52 |

TABLE 1-continued

A Summary of Examples 1–12.

| | Monomer | Crosslinkers | | | | Initiator | | Properties | | | | |
|---|---|---|---|---|---|---|---|---|---|---|---|---|
| No. | PEA | BPDMA | BPMA | BPEA | BPPDA | AIBN | RI | Tg (° C.) | Shore A | Tensile (psi) | % Elongation | Tear (lbf/in) |
| 11 | 99.00% | 1.00% | | | | 0.10% | 1.556 | | 17 | 196 | 246 | 37 |
| 12 | 99.50% | 0.50% | | | | 0.10% | 1.556 | | 14 | 309 | 309 | 34 |

\* PEA—Ethylene glycol phenyl ether acrylate
\* BPDMA—Bisphenol A ethoxylate (2 EO/phenol) dimethacrylate
\* AIBN—Azobisisobutyronitrile
\* BPMA—Bisphenol A dimethacrylate
\* BPPDA—Bisphenol A propoxylate (2 EO/phenol) diacrylate
\* The glass transition temperature of the homopolymer of ethylene glycol phenyl ether acrylate is −22° C.

EXAMPLE 13

A variety of acrylic IOLs having different dioptic powers were made from the exemplary stably elastic, high refractive index, low tack, optically clear homopolymers of the present invention detailed in Examples 1–12. Each lens was formed by injection or compression molding mixtures or pre-gels of the exemplary monomers, crosslinkers and optional additives of the present invention at a temperature of approximately 65° C. for about 16 hours followed by heating to approximately 120° C. for an additional 8 hours. Next, the molds were placed on a hot plate at approximately 55° C. for at least 10 minutes. Potentially toxic residues were extracted from the finished lenses with isopropyl alcohol under soxhelting conditions for 5 hours. Next the lenses were cooled and air dried in a forced air oven at room temperature for 24 hours. Final drying was accomplished in a vacuum oven under a reduced atmosphere at 45° C. for another 4 hours followed by heating the lenses at 75° C. for 24 hours. The resulting stably elastic homopolymer acrylic IOLs were soft, had non-tacky surfaces, were easily folded or rolled and had refractive indices ranging from about 1.556 to 1.559. Each of these IOLs was configured as a biconvex optic lens with a 0.5 mm edge thickness, a 0.6–1.2 mm center thickness, and a 6.0 mm diameter. Depending on the respective center thickness, each lens provided vision corrections ranging from 6 to 30 diopter.

In sum, it will be appreciated by those skilled in the art that the present invention addresses the long felt need of providing soft, stable, elastic, biocompatible, low tack, high refractive index, optically clear materials that are well suited to the production of medical devices including optical implants and overlays such as IOLs, corneal implants and corneal overlays, glaucoma shunts, contact lenses, and phakic lenses. Unlike the prior art copolymer compounds which utilize traditional crosslinking materials to produce soft copolymers with limited combinations of physical properties, these previously unobtainable combinations of desirable physical and chemical properties existing in a single composition are produced in accordance with the teachings of the present invention through the utilization of unique, stable elasticity inducing crosslinker compounds to modify acrylic homopolymers so that the resultant modified homopolymers possess and exhibit these often conflicting combinations of properties. The present invention not only produces these novel compounds for the first time, but does so in a greatly simplified manner that can be readily adapted and adjusted to produce any of a wide variety of compounds having specific combinations of physical and chemical properties, as desired. These compounds facilitate the production of improved medical devices and implants that are relatively inexpensive and easy to manufacture and manipulate during processing and during subsequent surgical implantation procedures as well. Moreover, they are particularly well suited for the manufacture of improved intraocular lenses that are true small incision lenses.

While the present invention has been described with respect to various specific examples and embodiments, it is to be understood that the present invention is not limited to these specific exemplary embodiments. Rather, the present invention can be modified by substituting additional, differing monomers and crosslinkers to produce additional modified homopolymers within the scope and teachings thereof. Further, differing methods can be used to produce the homopolymers of the present invention, and the resultant homopolymers can be configured into different articles and devices. Thus, the present invention is limited only by the following claims and can be variously practiced within the scope of these claims.

We claim:

1. An optical implant formed from an optically clear, high refractive index, and low-tack polyacrylate homopolymer comprising about 95% to 99.5% by weight monomer and from 0.5% to 5.0% by weight stable elasticity inducing crosslinker having a rigid chemical group disposed between a plurality of polymerizable, ethylenically unsaturated chemical groups, wherein said monomer is selected from the group consisting of phenoxyethyl acrylate, 2-phenoxyethyl acrylate, poly(ethylene glycol) phenyl ether acrylate, 3-phenoxypropyl acrylate, 2-phenoxypropyl acrylate, 4-phenoxybutyl acrylate, 3-phenylpropyl acrylate, and 4-phenylbutyl acrylate, and wherein said crosslinker is selected from the group consisting of bisphenol A ethoxylate (1EO/phenol) dimethacrylate, bisphenol A ethoxylate (2EO/phenol) diacrylate, bisphenol A ethoxylate (2EO/phenol) dimethacrylate, bisphenol A propoxy (2PO/phenol) diacrylate, bisphenol A propoxy (2PO/phenol) dimethacrylate, 2,2' diallylbisphenol diacrylate, 2,2' diallylbisphenol dimethacrylate, bis(4(2-acryloethoxy)phenyl) methane diacrylate, bis(4-(2-acryloethoxy)phenyl)methane dimethacrylate, bis(naphthol) A ethoxlate (X EO/naphthol) diacrylate, bis(naphthol) A ethoxlate (X EO/naphthol) dimethacrylate, bis(2-acryloalkylphenyl)propane diacrylate, bis(2-acryloalkylphenyl)propane dimethacrylate, 3,3'-(ethylenedioxy)diphenyl diacrylate, 3,3'-(ethylenedioxy) diphenyl dimethacrylate, naphthdiol A ethoxylate (X EO/naphthalene) diacrylate, and naphthdiol A ethoxylate (X EO/naphthalene) dimethacrylate, wherein X=1–5.

2. The optical implant of claim 1, further including a UV absorber.

3. The optical implant of claim 2, wherein said UV absorber is selected from the group consisting of acrylate, methacrylate, and vinyl functionalized benzophenones and benzotriazoles.

4. The optical implant of claim 1, wherein said optical implant is an intraocular lens.

5. The optical implant of claim 1, wherein said intraocular lens has a tapering peripheral border forming an edge having a thickness of approximately 0.5 mm or less.

6. The optical implant of claim 1, wherein said optical implant is a corneal implant.

7. The optical implant of claim 1, wherein said optical implant is a phakic lens.

* * * * *

UNITED STATES PATENT AND TRADEMARK OFFICE
CERTIFICATE OF CORRECTION

PATENT NO. : 6,780,899 B2
DATED : August 24, 2004
INVENTOR(S) : Xiugao Liao and Vijay Gulati It is certified that error appears in the above-identified patent and that said Letters Patent is hereby corrected as shown below:

Column 18,
Line 14, first word "LEO/phenol" should be -- 1EO/phenol --.

Signed and Sealed this

Thirtieth Day of November, 2004

JON W. DUDAS
*Director of the United States Patent and Trademark Office*